(12) United States Patent
Collier et al.

(10) Patent No.: US 7,335,221 B2
(45) Date of Patent: Feb. 26, 2008

(54) SUTURE ANCHORING AND TENSIONING DEVICE AND METHOD FOR USING SAME

(75) Inventors: John Collier, Franklin Lakes, NJ (US); Etan S. Chatlynne, Brooklyn, NY (US); Robert Nering, Stockton, NJ (US); Irene Nozad, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 273 days.

(21) Appl. No.: 10/122,970

(22) Filed: Apr. 12, 2002

(65) Prior Publication Data

US 2003/0195562 A1    Oct. 16, 2003

(51) Int. Cl.
*A61B 17/04* (2006.01)
(52) U.S. Cl. .................. 606/232; 606/148
(58) Field of Classification Search ............ 606/232, 606/233, 108, 216, 153, 155; 623/1.13, 1.23; 128/898
See application file for complete search history.

(56) References Cited

U.S. PATENT DOCUMENTS

| | | | |
|---|---|---|---|
| 4,901,721 A * | 2/1990 | Hakki | 606/232 |
| 5,078,731 A | 1/1992 | Hayhurst | |
| 5,123,914 A * | 6/1992 | Cope | 606/232 |
| 5,219,359 A | 6/1993 | McQuilkim et al. | |
| 5,232,204 A | 8/1993 | Nunez | |
| 5,376,101 A | 12/1994 | Green et al. | |
| 5,383,905 A | 1/1995 | Golds et al. | |
| 5,391,173 A | 2/1995 | Wilk | |
| 5,409,499 A | 4/1995 | Yi | |
| 5,474,572 A | 12/1995 | Hayhurst | |
| 5,514,159 A | 5/1996 | Matula et al. | |
| 5,520,702 A | 5/1996 | Sauer et al. | |
| 5,537,776 A | 7/1996 | Gilard, Sr. | |
| 5,630,824 A | 5/1997 | Hart | |
| 5,643,295 A * | 7/1997 | Yoon | 606/232 |
| 5,645,553 A | 7/1997 | Kolesa et al. | |
| 5,662,683 A | 9/1997 | Kay | |
| 5,681,351 A | 10/1997 | Jamiolkowski et al. | |
| 5,728,116 A * | 3/1998 | Rosenman | 606/232 |
| 5,741,301 A | 4/1998 | Pagedas | |
| 5,810,853 A | 9/1998 | Yoon | |
| 5,810,882 A | 9/1998 | Bolduc et al. | |
| 5,849,019 A | 12/1998 | Yoon | |
| 5,919,208 A | 7/1999 | Valenti | |
| 5,976,159 A | 11/1999 | Bolduc et al. | |
| 6,001,110 A | 12/1999 | Adams | |
| 6,015,428 A | 1/2000 | Pagedas | |
| 6,039,176 A | 3/2000 | Wright | |
| 6,066,160 A | 5/2000 | Colvin et al. | |
| 6,074,409 A | 6/2000 | Goldfarb | |

(Continued)

FOREIGN PATENT DOCUMENTS

EP    0 663 184 A1    7/1995

(Continued)

*Primary Examiner*—Glenn K. Dawson
(74) *Attorney, Agent, or Firm*—Greenberg Traurig, LLP

(57) ABSTRACT

A suture anchoring device is made from a coiled member having a helical configuration with a multiplicity of turns. When used in connection with a surgical procedure, the device is positioned adjacent to a wound site and a suture is attached to at least two of the turns so as to anchor the suture to the coiled member.

10 Claims, 17 Drawing Sheets

U.S. PATENT DOCUMENTS

| | | |
|---|---|---|
| 6,099,553 A | 8/2000 | Hart et al. |
| 6,106,545 A | 8/2000 | Egan |
| 6,126,677 A | 10/2000 | Ganaja et al. |
| 6,165,204 A | 12/2000 | Levinson et al. |
| 6,200,329 B1 | 3/2001 | Fung et al. |
| 6,231,592 B1 | 5/2001 | Bonutti et al. |
| 6,293,961 B2 | 9/2001 | Schwartz et al. |
| 6,428,550 B1 | 8/2002 | Vargas et al. |
| 6,599,311 B1 * | 7/2003 | Biggs et al. ............... 606/232 |
| 6,626,917 B1 | 9/2003 | Craig |
| 6,652,562 B2 * | 11/2003 | Collier et al. ............... 606/232 |
| 2006/0004410 A1 * | 1/2006 | Nobis et al. ............... 606/232 |
| 2007/0083235 A1 * | 4/2007 | Jervis et al. ............... 606/232 |

FOREIGN PATENT DOCUMENTS

| | | |
|---|---|---|
| WO | WO 00/28902 | 5/2000 |
| WO | WO 01/45570 A1 | 6/2001 |
| WO | WO 01/45571 A1 | 6/2001 |

* cited by examiner

Y= SUTURE IS COMING FROM THE INTERIOR SIDE OF THE HELIX TO THE EXTERIOR SIDE OF THE HELIX

X= SUTURE IS GOING FROM THE EXTERIOR SIDE OF THE HELIX TO THE INTERIOR SIDE OF THE HELIX

SUTURE ANCHORING AND TENSIONING DEVICE AND METHOD FOR USING SAME

FIELD OF THE INVENTION

The present invention relates to a suture anchoring and tensioning device for use with sutures in surgical procedures.

BACKGROUND OF THE INVENTION

In surgical procedures sutures are commonly used to close incisions and to reunite damaged tissue. Typically, the sutures are maneuvered and passed through the affected tissue and the free ends of the sutures are individually tied together by the surgeon. In most surgical incisions, the surgical site area is sufficiently exposed to permit the surgeon to access and quickly tie the suture manually with a surgical knot. However, in other surgical procedures, such as endoscopic procedures, laparoscopic procedures, arthroscopic procedures and the like, or when robotic surgical procedures occur, the suturing site is inaccessible to the surgeon's hands. As a result, the surgeon must tie each of the suture ends into a knot at location remote from the suturing site, and then manipulate suitably configured instruments for sliding the surgical knot to the suturing site of the incision. Further, surgeons may tie surgical knots intracorporeally (inside of the body) using surgical tools to tie the knot down to the tissue. Conventionally, most surgical sutures are secured with surgical knots that are somewhat cumbersome and slow to tie. As a result, knot tying is one of the more time-consuming steps in the suturing process of the surgical procedure. Also, it is noted that knots are weak points in a suture. That is to say, when a knotted suture is broken from applied tension (assuming the suture is otherwise free from imperfections), the suture will break at the knot.

In the foregoing circumstances, there remains a need for the elimination of knot tying from surgical procedures in order to significantly reduce the time duration of surgical operations. This is especially true with regard to minimally invasive surgical procedures where the tying of surgical knots within confined spaces is extremely difficult and time consuming. The present invention pertains to a helical suture anchoring device that would be applied quickly and would apply sufficient tension to the sewn sutures (including monofilament sutures) in order to restrict movement of the sutures at the surgical site.

DISCUSSION OF RELATED ART

Suture locking devices such as suture clips, surgical fasteners, hinged clips, suture terminating devices, hemostatic clips, and suture fixation devices of various configurations, designs, structures and materials of construction are well known in the prior art. For example, U.S. Pat. No. 6,165,204 to Levinson, et al. discloses a shaped suture clip having a pair of plates joined together at one end to form a corner point (vertex) having an acute angle and having, at the other end, a pair of hook members, so as to clamp the suture in place. The opening of the clamp is slightly smaller than the diameter of the suture, thereby resulting in a pressure hold when the suture is passed through the suture clip. This suture clip will, however, only clamp one end of the suture in place.

U.S. Pat. No. 5,474,572 to Hayhurst and U.S. Pat. No. 5,645,553 to Kolesa et al. disclose the use of a hinged clip that snaps closed after the suture threads are placed within the (jaws) holding members. The hinge clip is then snapped into place such that the suture is held transversely across the holding members, thus locking the suture in place. There is a possibility of not achieving a good set, as the snap may not have been properly actuated, or it may have been inadvertently released.

U.S. Pat. No. 6,001,110 to Adams discloses a hemostatic clip having pseudoelastic properties at body temperature. The pseudoelastic NITINOL® clips are used to cause hemostatsis of blood vessels located along the gastrointestinal tract. The hemostatic clip, which has a first configuration that is useful for ligating blood vessels, can be deformed to a second configuration to facilitate placement to a desired location within the body.

U.S. Pat. No. 6,106,545 to Egan discloses a suture tensioning and fixation device, which includes the combination of a plurality of suture retaining elements and a suture thread. The suture thread engages portions of each of the retaining elements, such that the suture thread is adapted to functionally engage the retaining elements for holding the interwoven suture segments in place for a knotless joint.

U.S. Pat. No. 6,066,160 to Colvin, et al. discloses a suture terminator device for enhanced tissue securing used in minimally invasive surgery. The suture securing device includes a pair of locking apertures for engaging a portion of a suture at its threaded end.

U.S. Pat. No. 5,537,776 to Gilard, Sr. discloses a fishing line connector having a shank, a coiled member and an open-ended eye loop. The coiled member includes a series of contiguous helical coils arranged in a spaced longitudinal relationship. The fishing line connector provides a knotless connection for a fishing line when the line is wrapped around the helical coiled member in alternating longitudinal directions and snapped into the open-ended eye loop.

In view of the prior art discussed hereinabove, it is an object of the present invention to provide a helical suture anchoring and tensioning device that allows the surgeon to feel the amount of tension applied to the suture.

Another object of the present invention is to provide a helical suture anchoring device that eliminates manual knot tying by the surgeon performing the surgical procedure.

Another object of the present invention is to provide a helical suture anchoring device that is suitable for a wide variety of sutures (i.e., such as monofilament and braided sutures).

Another object of the present invention is to provide a helical suture anchoring device that is at least as strong as conventional surgical knots.

Yet another object of the present invention is to provide a helical suture anchoring device that is small so as not to interfere with adjacent suture ties.

A still further object of the present invention is to provide a helical suture anchoring and tensioning device that is simple to use, and would require only minimal training by the surgeon.

SUMMARY OF THE INVENTION

In accordance with the present invention, there is provided a novel suture anchoring device which overcomes the problems and shortcomings of the prior art devices discussed hereinabove. More particularly, the novel suture anchoring device includes a coiled member having a helical configuration. In one embodiment, the coiled member includes a multiplicity of turns which form a descending spiral. The helical configuration can have a geometrical shape or non-geometrical shape. When used in connection with a surgical procedure, the device is positioned adjacent to a suturing site and a suture is attached to at least two of the turns so as to anchor the suture to the coiled member.

BRIEF DESCRIPTION OF THE DRAWINGS

Further objects, features and advantages of the present invention will become apparent upon consideration of the following detailed description of various exemplary embodiments considered in connection with the accompanying drawings, in which.

DETAILED DESCRIPTION OF THE EXEMPLARY EMBODIMENTS

Figure 1:
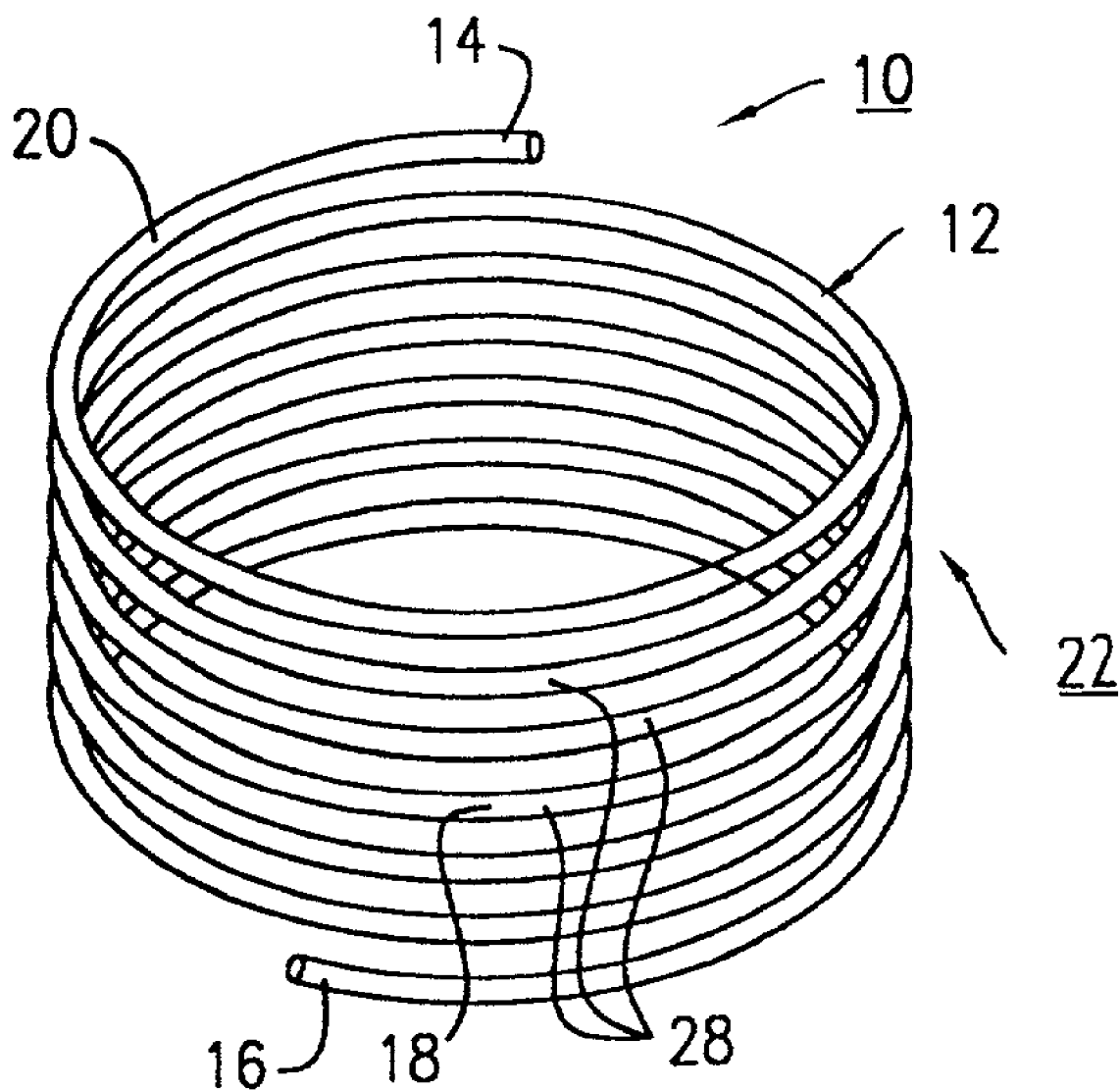
FIG. 1 is a perspective view of a helical suture anchoring device constructed in accordance with a first exemplary embodiment of the present invention, the device being shown in a coiled configuration and without a suture.

Referring to FIGS. 1 through 5b, there is shown a helical suture and anchoring tensioning device 10 for use in surgical procedures. The device 10, as shown in FIG. 1, includes a coiled, circularly-shaped, thin rod or member 12 having a distal end 14, a proximal end 16, a center point 18 between the distal and proximal ends 14, 16 and an outer wall surface 20. As shown in FIG. 1, device 10 is in its normally coiled helical configuration 22, wherein its coiled helical rod or member 12 includes a plurality of helically-configured coiled turns 28. As used herein, the term "coiled helical configuration" shall define any spiral configuration having a plurality of descending turns, regardless of its geometrical or non-geometrical shape. A geometrical shape is any shape which is conducive to a description using conventional geometry nomenclature. Examples of suitable geometrical shapes include, but are not limited to, the following: circular, oval, elliptical, conical, rectangular, square, triangular, pyramidal and any other polygonal shape. A non-geometrical shape is any shape which is not conducive to a description using conventional geometry nomenclature. Examples of suitable non-geometrical shapes include, but are not limited to, the following: U-shaped, V-shaped, parabolically-shaped and the like.

Figure 2A:
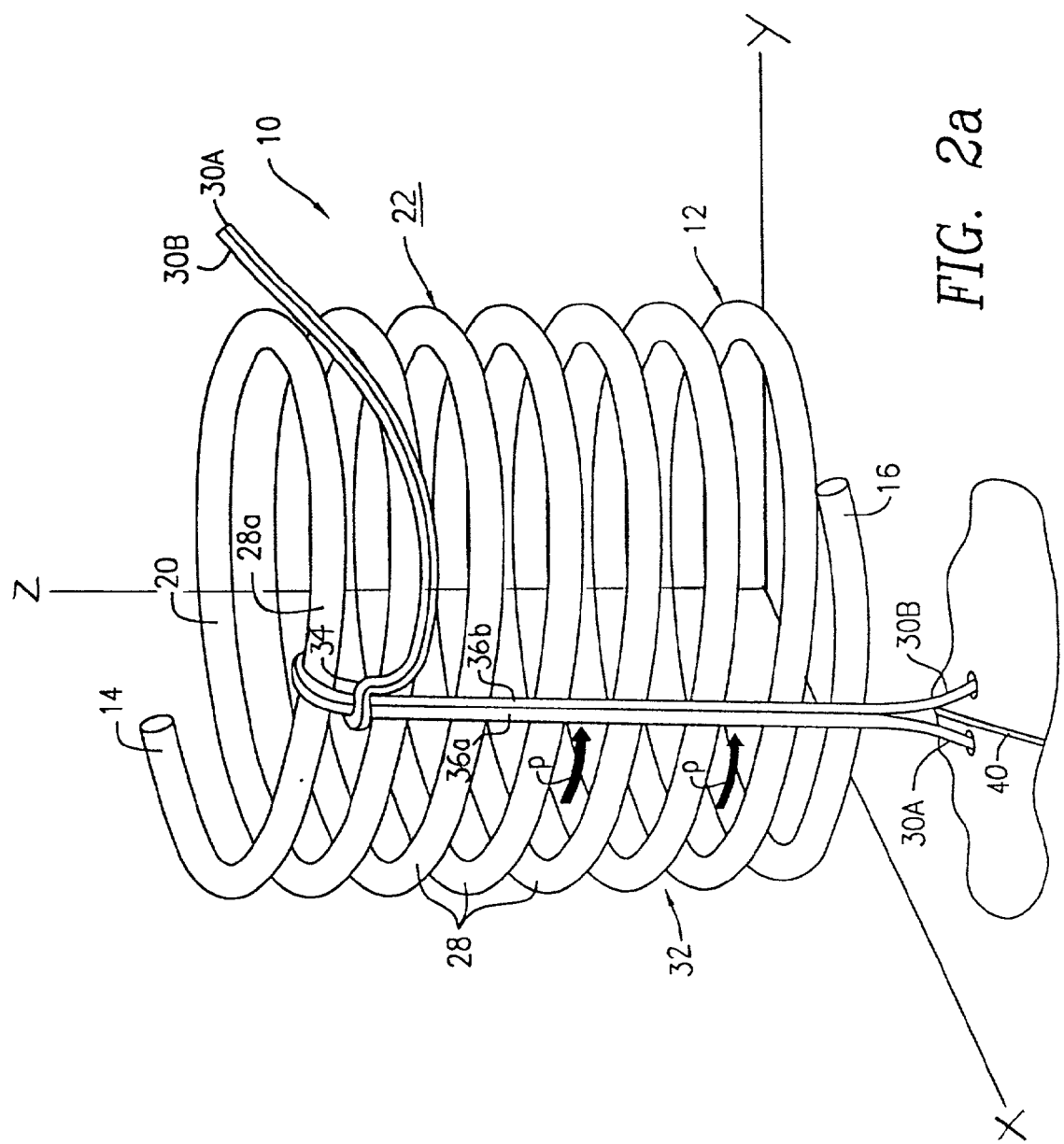
FIGS. 2a to 2c are schematic representations which illustrate the steps involved in the attachment of two suture ends to the helical suture anchoring device of FIG. 1 for suturing an incision by a surgeon.

The helical suture anchoring device (helical suture lock) 10 can be used in combination with multiple sutures 30A, 30B (see FIG. 2c) or with a single suture 30 (see FIG. 3) for various types of surgical procedures by surgeons (to be discussed hereinafter in the "in operation" sections). The single suture 30 or the multiple sutures 30A, 30B may wind down the helical path P in either a clockwise or counter-clockwise rotation depending upon the orientation of the helically-configured coiled turns 28 and the lashing methods employed, as described hereinafter. The coiled member 12 may be fabricated and coiled, preferably, from any biocompatible medical material, such as a polymeric, metallic or superelastic (e.g., a nickel-titanium alloy having a memory shape, such as NITINOL®) material that can be coiled into a tight spiral and helical configuration having an inherent resiliency, as depicted in FIGS. 1, 2a and 3. The polymeric material may be absorbable within a mammalian body, or it may be non-absorbable.

If the helical suture anchoring and tensioning device 10 is made from a nickel-titanium alloy having memory shape capabilities (such as NITINOL® ALLOYS—SES08 ), one method of manufacturing the device 10 starts with the provision of a thin elongated rod having a thickness in a range of from about 0.15 mm to about 4.0 mm and a length in a range of from about 10.0 mm to about 50.0 mm. The rod is then coiled into a tight spiral having a helical diameter in a range of from about 1.0 mm to about 5.0 mm. A fixturing/clamping device and/or mandril (not shown) is used to maintain the coiled configuration of the rod. The coiled rod and clamping device are then placed in a heat treatment apparatus (e.g., a furnace or salt bath) and heated to a temperature in a range of from about 450° C. to about 600° C., but preferably to a temperature in a range of from about 500° C. to about 550° C. Upon reaching the proper shape-setting temperature (i.e., approximately 500° C.), the rod will become set in its coiled helical state. Typically, the heat treatment process lasts for a period of time in a range of from about 2 minutes to about 30 minutes, but more preferably for a period of time in a range of from about 2 minutes to about 15 minutes. The heat-treated rod and clamping device are then removed from the heat treating equipment. After removal from the clamping device, the coiled helical rod is quenched in water or cooled down rapidly with chilled air.

Figure 2B:
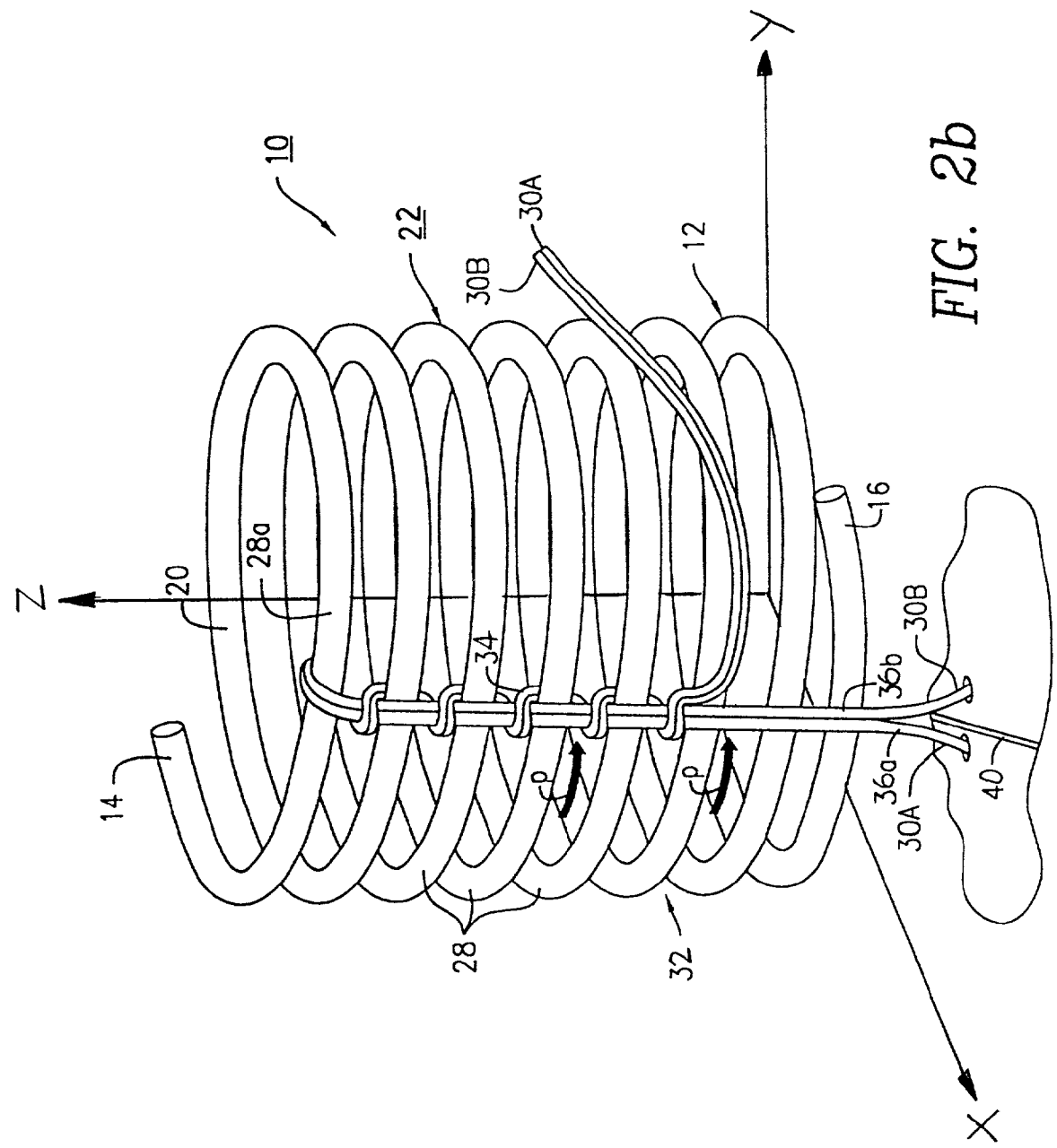
Figure 2C:
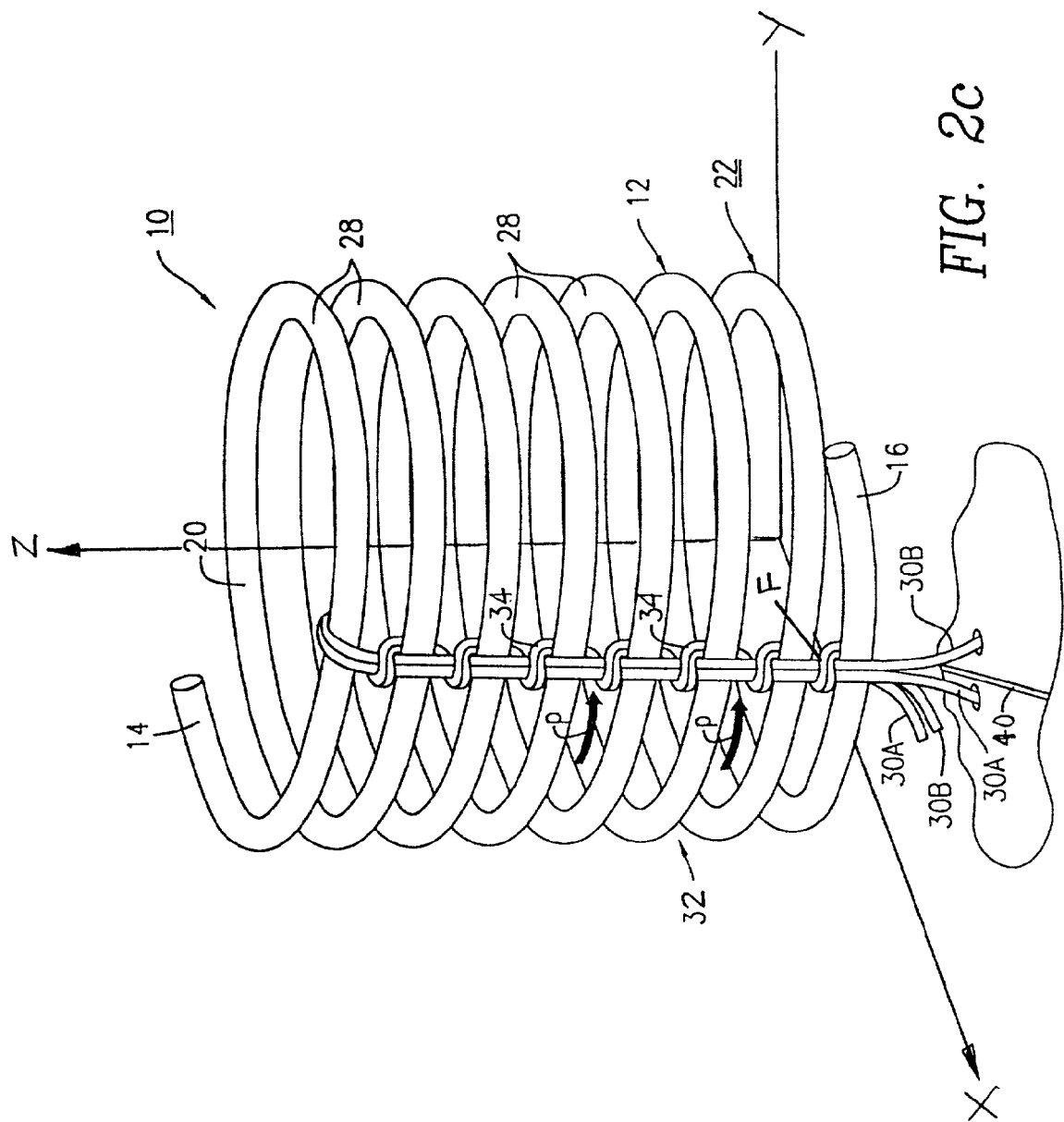
Figure 3:
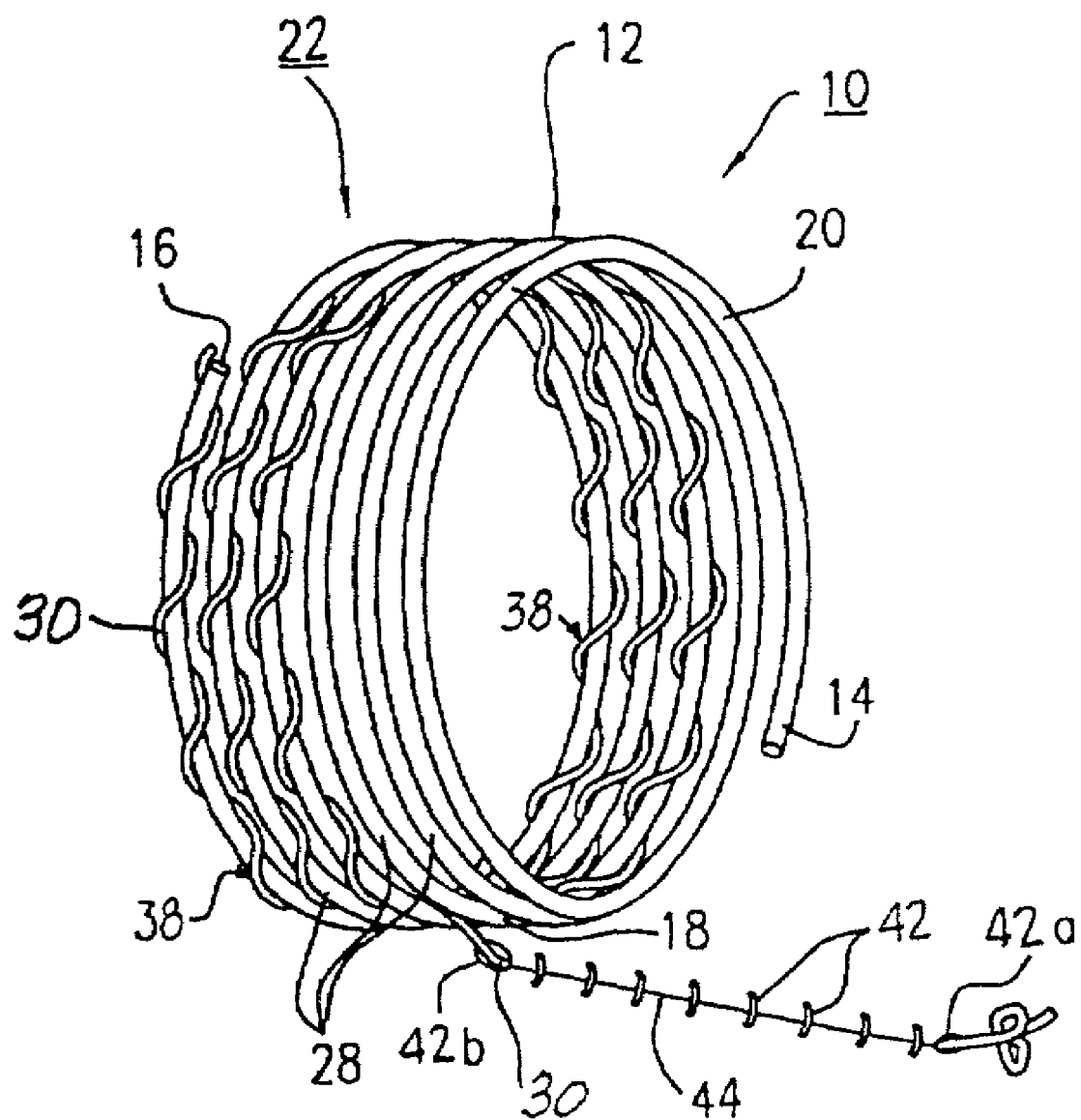
FIG. 3 is a perspective view of the helical suture anchoring device of FIG. 1 showing an alternate method of entwining a suture along the length of the helical coils for suturing an incision by a surgeon.

FIGS. 2a to 2c demonstrate the steps involved for attaching a pair of sutures 30A and 30B to the helical suture anchoring device 10. As shown in FIG. 2a, the device 10 is in its coiled helical configuration 22 wherein the sutures 30A, 30B are positioned parallel to the longitudinal Z-axis of the coiled helix along an outer side 32 of the helically coiled turns 28. In FIGS. 2a and 2c the Z-axis is approximately perpendicular to the wound site. The sutures 30A, 30B are then looped over the first coiled turn 28a. The initial loop over by sutures 30A, 30B does not have to start at the first (uppermost) coiled turn 28a but may be initiated at lower (subsequent) coiled turns 28. Sutures 30A, 30B are then wound through each of the helically-configured coiled turns 28 such that sutures 30A, 30B are wound back down the coiled member 12 along the helical path P of device 10 in order to lash the sutures 30A, 30B to the device 10 (see FIG. 2c). As shown in FIG. 2c, sutures 30A, 30B are wrapped about each of the coiled turns 28 of the coiled member 12 such that sutures 30A, 30B are frapped about themselves in order to create a multiple frapping arrangement 34. This frapping process results when the sutures 30A, 30B are forced downward by each helically-coiled turn 28 where the sutures 30A, 30B catch upon portions or segments 36a, 36b of sutures 30A, 30B, respectively, that are positioned parallel to the longitudinal Z-axis of the coiled member 12, such that one frapping arrangement 34 occurs per revolution of sutures 30A, 30B about the Z-axis. The lashing of the sutures 30A, 30B to each of the turns 28 of the coiled member 12 negates the movement of sutures 30A, 30B. The frapping arrangement 34 (of sutures 30A, 30B) helps maximize the internal frictional forces F by removing slack from the sutures 30A, 30B, as depicted in FIG. 2c. The helically-configured coiled turns 28 of the coiled member 12 provides a guide to allow the surgeon to lash the sutures 30A, 30B to the helical suture anchoring device 10 with ease.

As used herein, the term "lashing" is defined as a binding with a suture used for fastening. A lashing is typically comprised of a combination of wrappings and trappings. A "wrapping", as used herein, is defined as a portion of a lashing which secures a section of suture(s) that are directly against and in contact with the suture anchoring and tensioning device. A "frapping", as used herein, is defined as a portion of a lashing which serves to remove slack from the lashing. This is accomplished by pulling one section of the suture(s) over other portions of the suture(s) that are in contact with each other.

FIG. 3 demonstrates another method of attaching a single suture 30 to the helical suture anchoring device 10. As shown in FIG. 3, the suture 30 is entwined between the center point 18 and the proximal end 16 of the coiled member 12 (or at any other point along the coiled member 12). The suture 30 is now entwined within the coiled member 12 along the multiple coiled turns 28. This is accomplished because the coiled member 12 has a resiliency sufficient to permit the coiled member 12 to be movable between an extended position, in which the spacing between adjacent pairs of coiled turns 28 is increased to facilitate the application of suture 30 to the coiled member 12, and a contracted position, in which the spacing between the adjacent pairs of the coiled turns 28 is decreased to facilitate the anchoring of suture 30 to the coiled member 12.

Figure 4A:
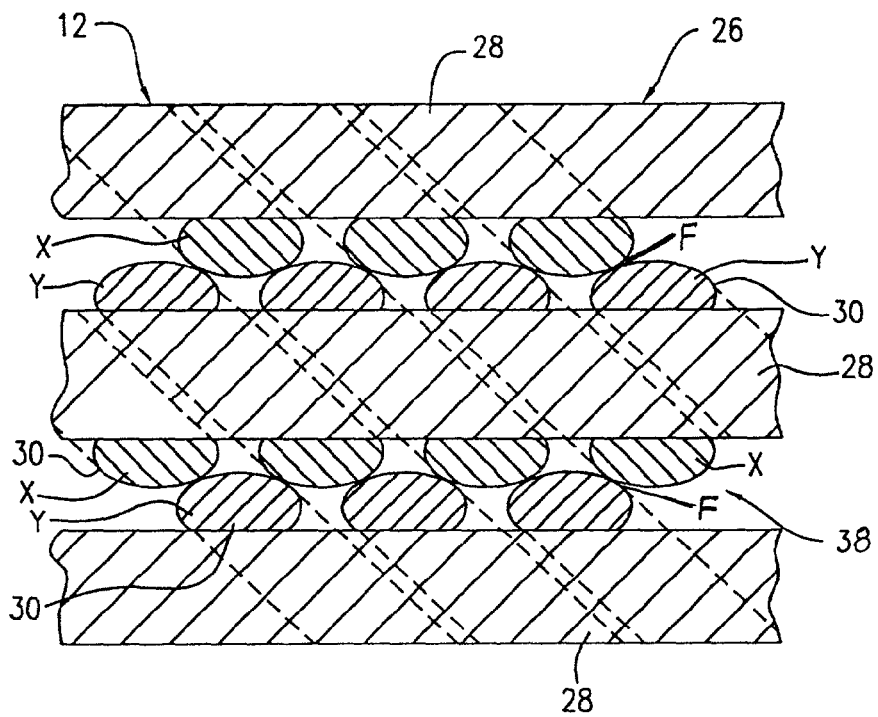
FIG. 4a is an enlarged cross-sectional planar projection of the helical suture anchoring device of FIG. 3 showing the entwining effect of the suture along the length of multiple helical coils.
Figure 4B:
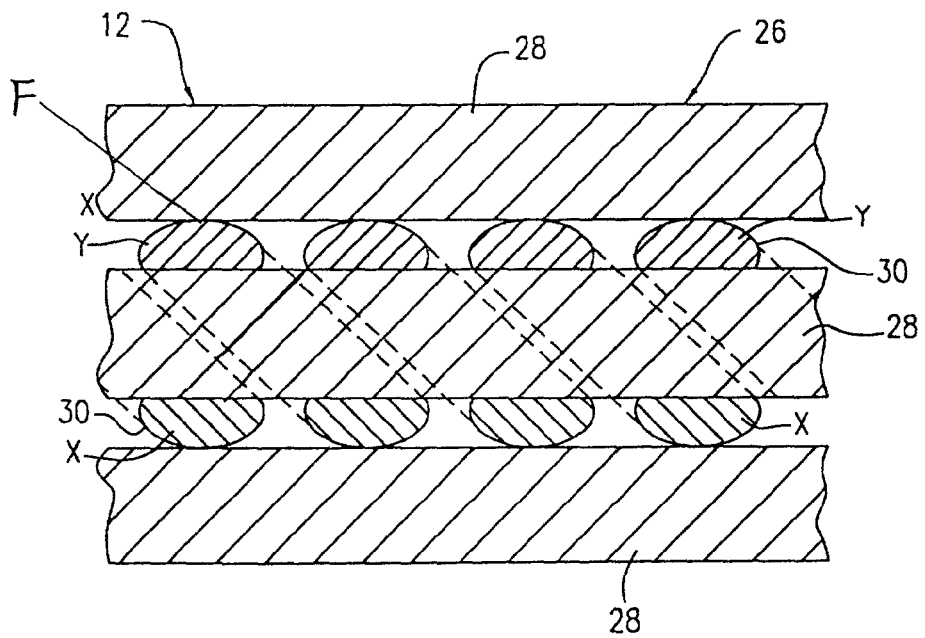
FIG. 4b is an enlarged cross-sectional planar projection of the helical suture anchoring device of FIG. 3 showing the entwining effect of the suture along the length of a single turn of the helical coil.

The result of the foregoing attachment method is that the single suture 30 forms a mesh formation 38, wherein the suture 30 is entwined around multiple coiled turns 28 and portions of suture 30 are pressed against neighboring suture portions 30, as long as the gaps between the coiled turns are less than the suture diameter, as shown in FIG. 4a. Even if only one coiled turn 28 was entwined with suture 30, the neighboring coiled turns 28 would apply friction forces F to suture 30, as depicted in FIG. 4b. In the aforementioned configurations (see FIGS. 4a and 4b), there are sufficient internal frictional forces F to restrict movement of suture 30 within the entwined multiple coiled turns 28, and thus, the device 10 is used in place of a surgical knot. Due to the nature of the aforementioned entwinement, the strength of the suture 30 is not significantly compromised (as in the case when the suture is secured with a surgical knot). Moreover, the resiliency of the coiled member 12 can be selected such that the coiled member 12 exerts a counteracting force on the suture 30 if it is attached to the coiled member 12 so as to cause its contraction, whereby the coiled member 12 facilitates tensioning of the suture 30.

Figure 5A:
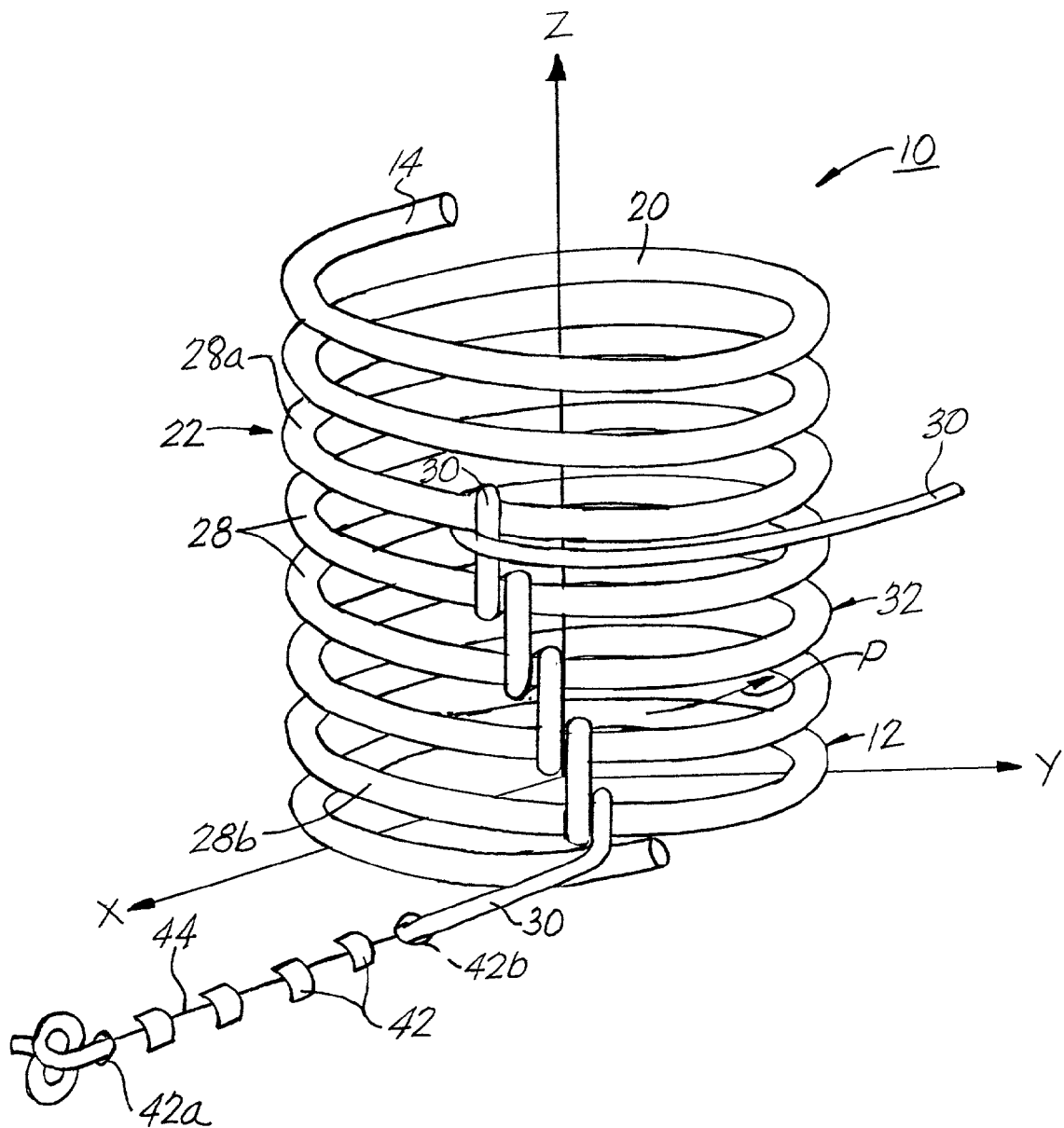
FIGS. 5a and 5b are schematic representations which illustrate the steps involved in yet another method of attachment of a single suture to the helical suture anchoring device of FIG. 1 for suturing an incision by a surgeon.
Figure 5B:
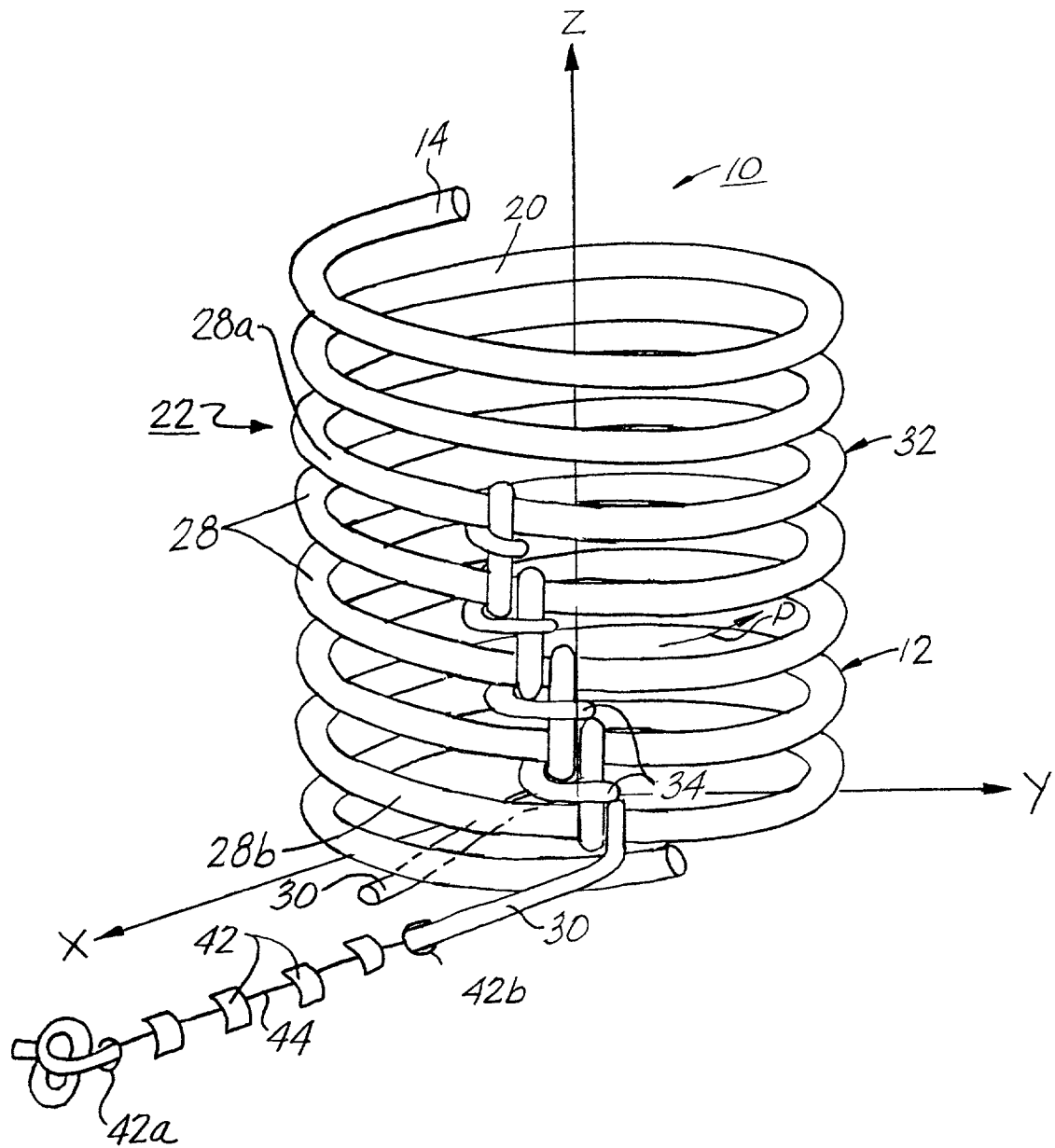

FIGS. 5a and 5b demonstrate yet another method of attaching a single suture 30 to the helical anchoring device 10 on an incision site 44 at the end stitch point 42b for a running stitch surgical procedure. With reference to FIG. 5a, the single suture 30 is initially looped over multiple helically-coiled turns 28 starting from the second lowest coiled turn 28b and subsequently looped over an upward coiled turn 28a (see FIG. 5a). This looping-over step does not have to go to the uppermost coiled turn 28, as the looping-over step could start on any of the upper coiled turns 28. The suture 30 is rotated in the sense of the downward path P while being moved away (upward) from the incision site 44. The suture 30 is then wound from the aforementioned coiled turns 28 (the upward position) of the uppermost coiled turn 28a through each of the helically-coiled turns 28 via the helical path P (downward) to the lowermost coiled turn 28b of device 10. As shown in FIG. 5b, the single suture 30 is frapped about its previously upwardly directed segment to form a lashing which is somewhat similar to the lashing of the first embodiment of the present invention, as shown in FIG. 2c.

In surgical operations, the helical suture anchoring device 10 can be used in combination with multiple sutures 30A, 30B or with a single suture 30 for various surgical procedures. For example, as illustrated in FIGS. 2a to 2c, the helical suture anchoring and tensioning device 10 is used to secure two sutures 30A and 30B at an incision site 40. Referring to FIG. 2a, the sutures 30A and 30B are in a parallel relationship (with each other) on the outer side 32 of the coiled turns 28 of the coiled member 12 as they (i.e., the sutures 30A and 30B) are looped over the first coiled turn 28a. FIG. 2b shows the sutures 30A and 30B being wound through the helical path P of each of the turns 28 of the coiled member 12, such that the sutures 30A and 30B are frapped about themselves to form the frapping arrangement 34. Sutures 30A and 30B are guided downward by each of the coiled turns 28 such that they (i.e., the sutures 30A and 30B) catch upon portions 36a, 36b of sutures 30A, 30B, respectively, to form the frapping arrangement 34 (of sutures 30A and 30B). FIG. 2c depicts the completed lashing of sutures 30A and 30B to the coiled member 12. This binding of sutures 30A and 30B to the device 10 restricts any movement of sutures 30A and 30B relative to the device 10 at the incision site 40, as shown in FIG. 2c. Thus, the sutures 30A and 30B are in a tensioned condition over the incision site 40.

In another example, as shown in FIG. 3, the helical suture anchoring and tensioning device 10 of the present invention may be used to secure a single suture 30 or multiple sutures, such as in surgical procedures involving a running stitch 42 on a wound at an incision site 44 where a beginning stitch 42a and an end stitch 42b are at different locations (see FIG. 3). Referring still to FIG. 3, the surgeon has entwined the single suture 30 along multiple coiled turns 28, which initiates the tensioning of suture 30 within the multiple coiled turns 28 of device 10. The device 10 is shown in its helically-coiled configuration 22, such that the entwined suture 30 is in a mesh-like formation 38 within the coiled turns 28. These coiled turns 28 exert a frictional force F on the entwined suture 30 (see FIG. 4a) in order to keep the suture 30 from moving. This in turn restricts the movement of suture 30 such that the device 10 is held in place at the end stitch 42b, as depicted in FIG. 3.

Figure 6:
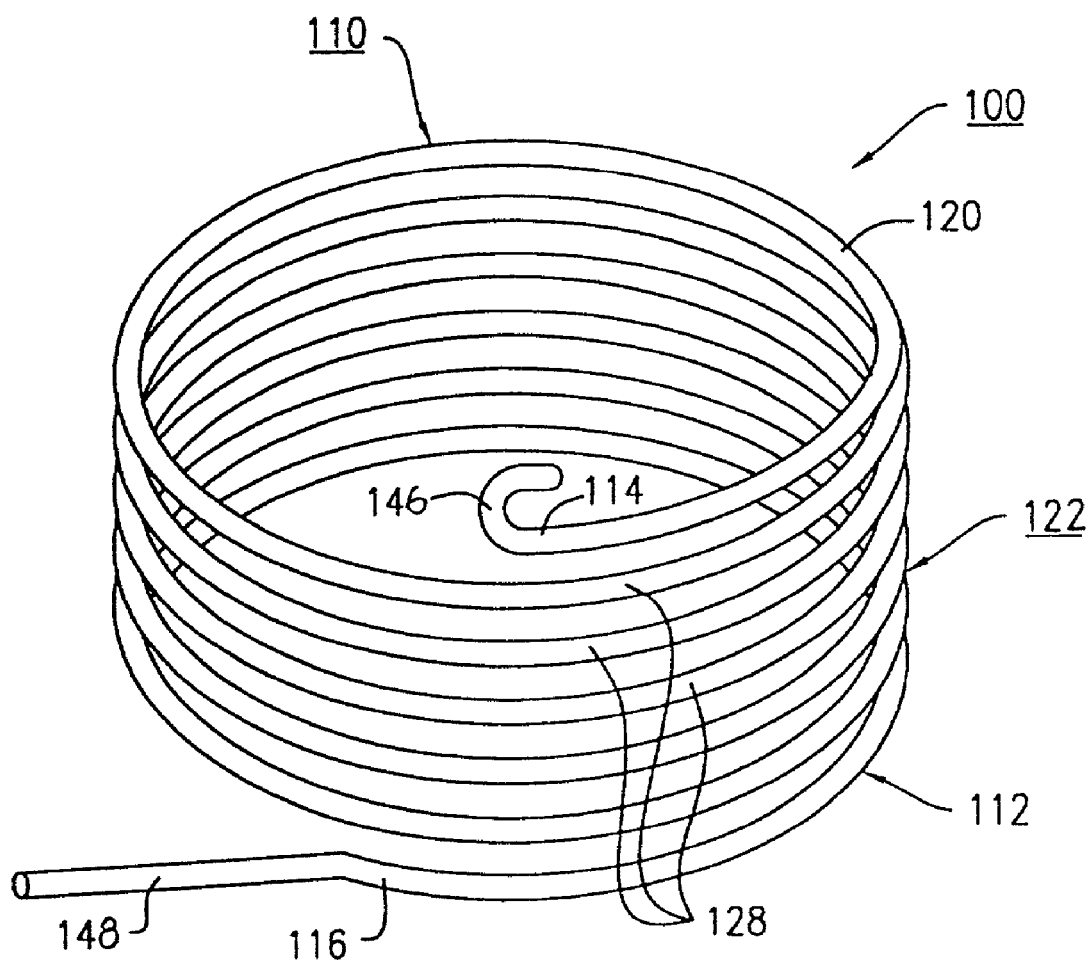
FIG. 6 is a perspective view of a helical suture anchoring device constructed in accordance with a second exemplary embodiment of the present invention, the device being shown in a coiled, circular-shaped configuration and without a suture.

A secondary exemplary embodiment of the present invention is illustrated in FIG. 6. Elements illustrated in FIG. 6 which correspond to the elements described above with reference to FIGS. 1, 2c and 3 have been designated by corresponding reference numbers increased by one hundred. The second embodiment is constructed and operated in the same manner as the first embodiment, unless it is otherwise stated.

Figure 7A:
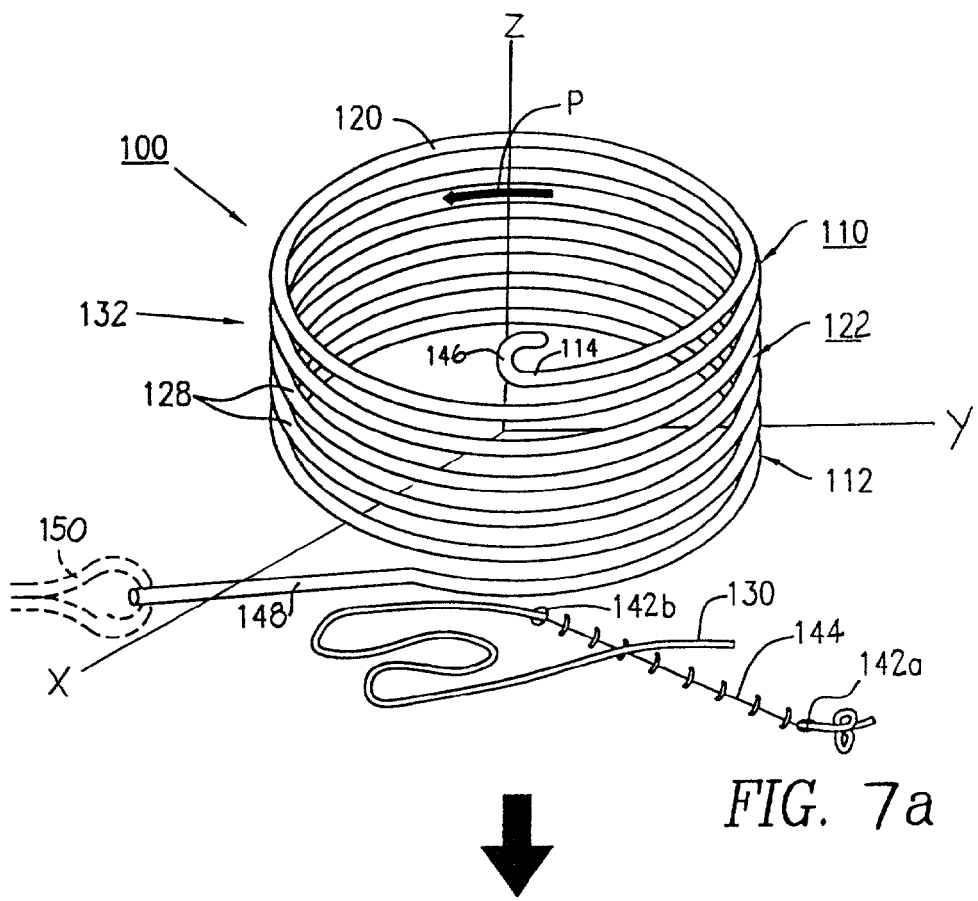
FIGS. 7a to 7f are schematic representations which illustrate the steps involved in the attachment of a single suture to the helical suture anchoring device of FIG. 6 for suturing an incision by a surgeon.
Figure 7B:
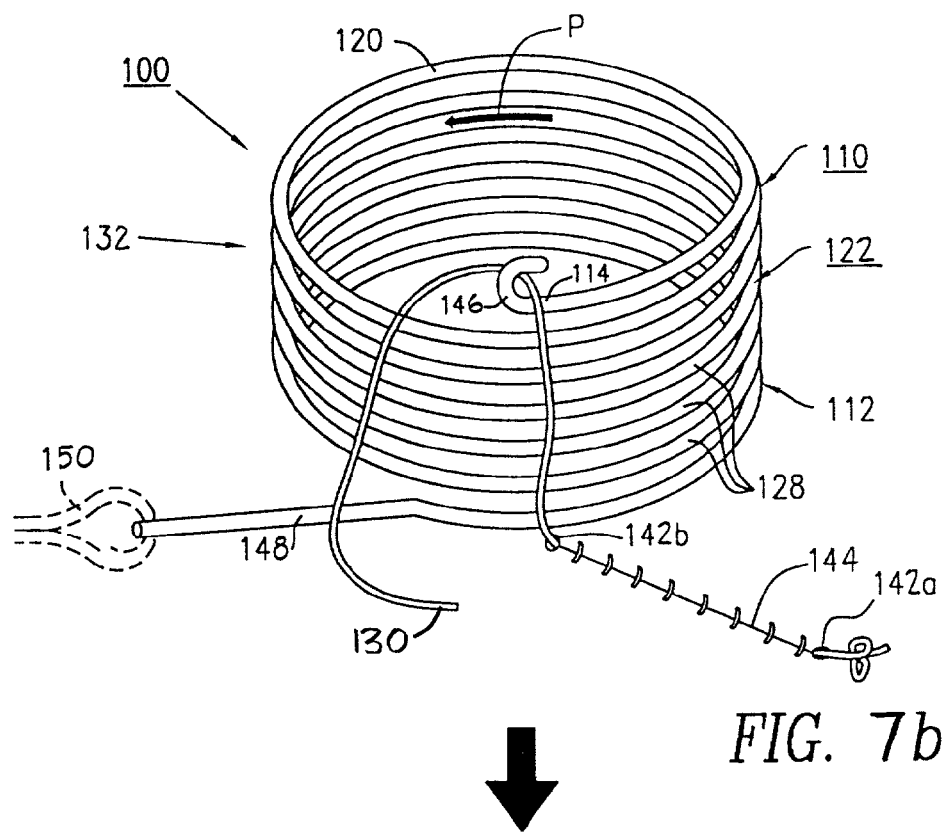

With reference to FIGS. 6, 7a and 7b, the helical suture anchoring and tensioning device 110 is in a coiled helical configuration 122. The distal end 114 includes a hook member 146 and the proximal end 116 includes an elongated and straight handle member 148. The hook member 146 is used for attaching a small section of a single suture 130 about the hook member 146 (see FIG. 7b). The handle member 148 is for holding the device 110 in a stationary position by the use of deployment aid 150 (i.e., a needle holder being shown in dotted). The remaining elements of the coiled member 112 of device 110 are exactly the same as the component elements of the device 10 of the first embodiment.

Figure 7C:
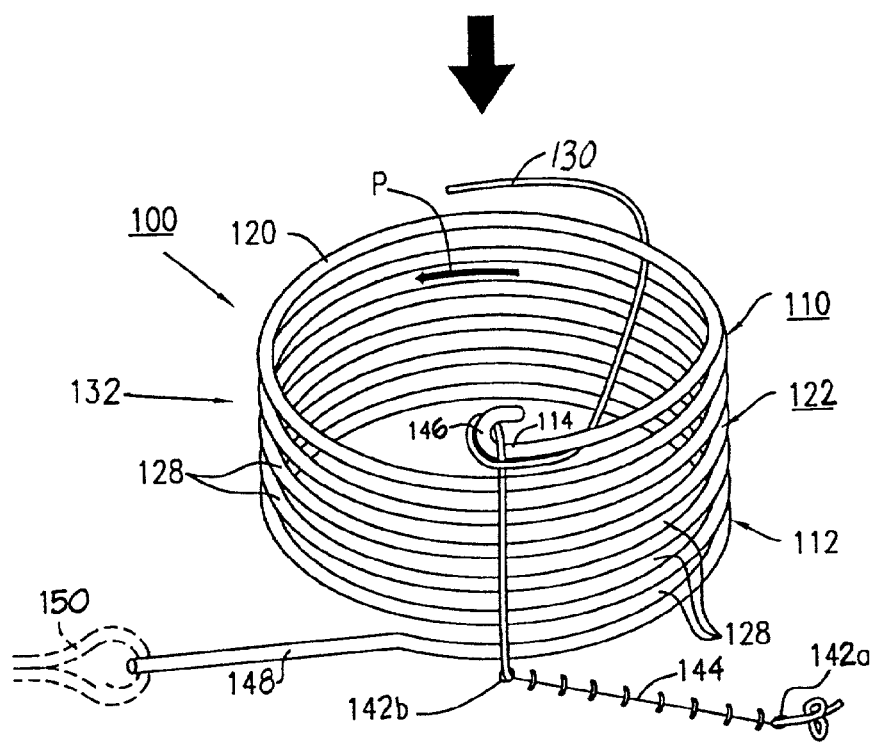
Figure 7D:
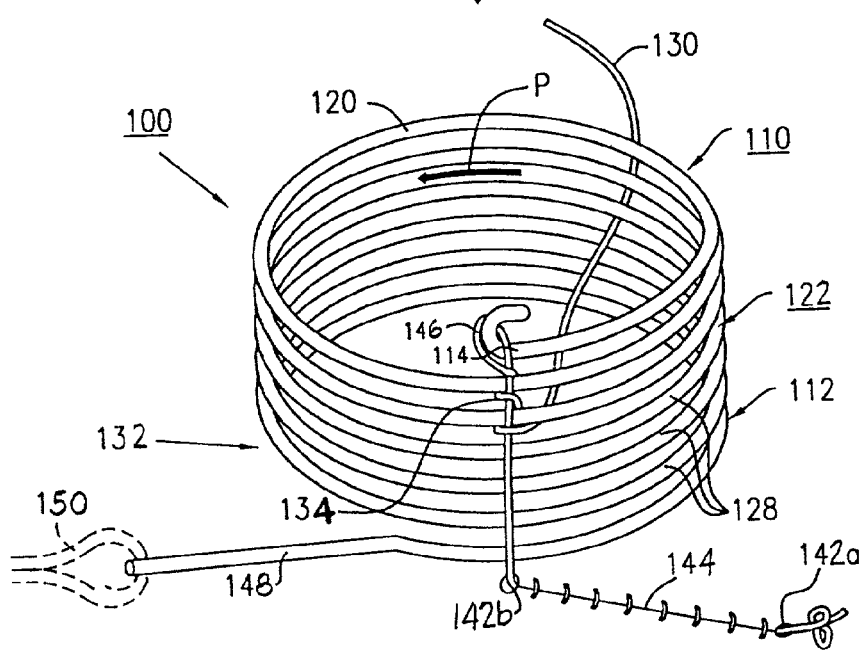
Figure 7E:
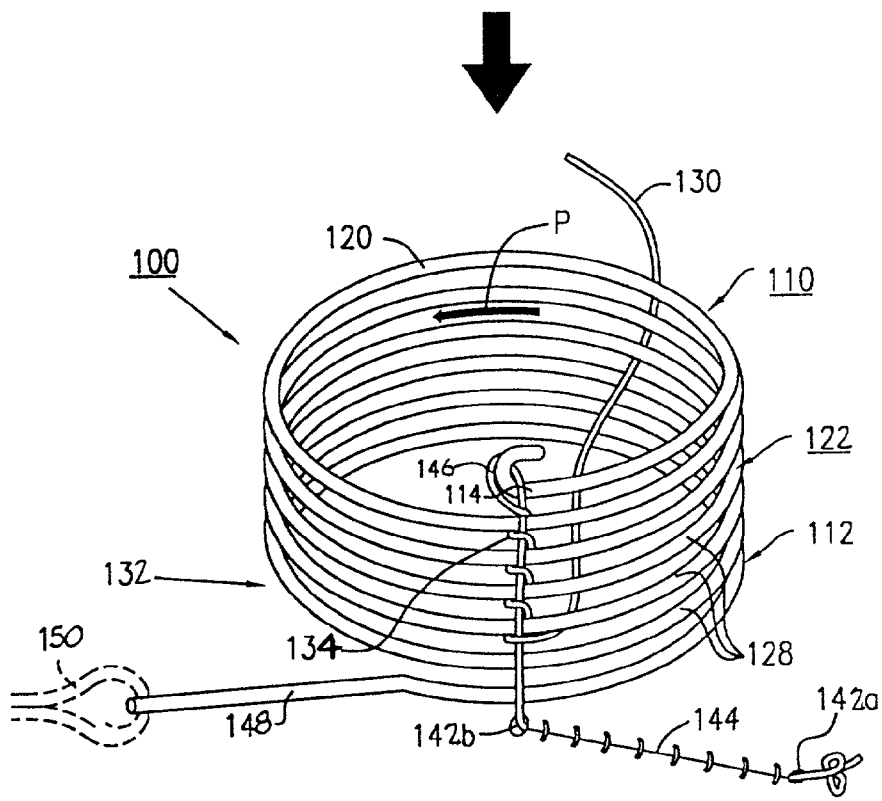
Figure 7F:
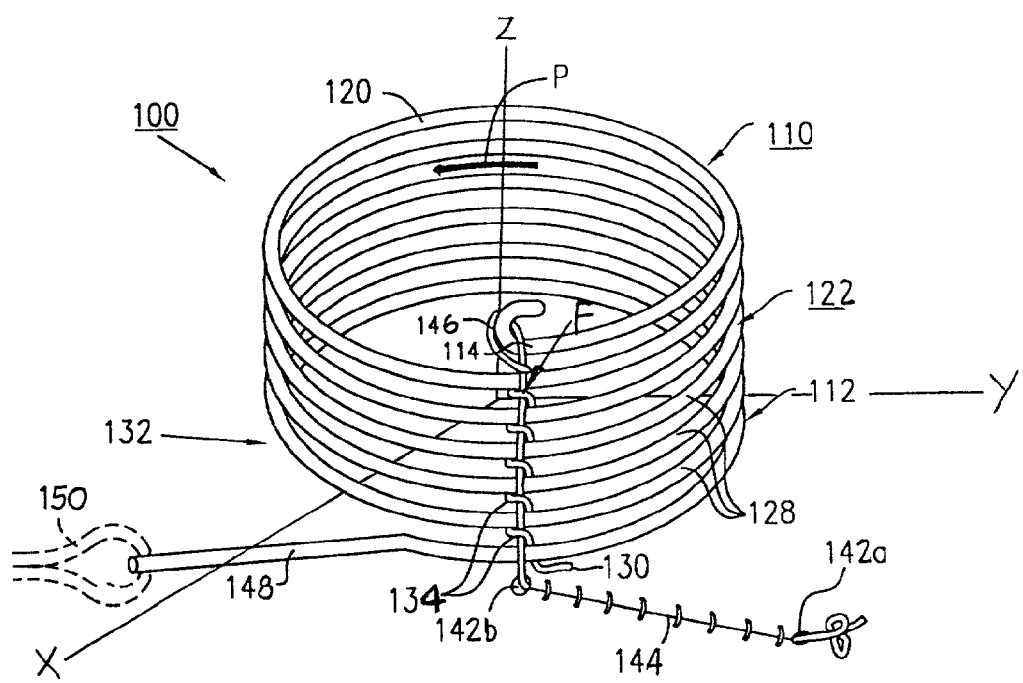

In operation, the helical suture anchoring and tensioning device 110 in combination with the suture 130 may be used in a surgical procedure as depicted in FIGS. 7a through 7f. For example, the device 110 is used for securing a single suture 130 on an incision site 144 at an end stitch point 142b for a running stitch surgical procedure. With reference to FIG. 7a, the device 110 is positioned and placed in close proximity to the end stitch point 142b on the incision site 144 for securing the single suture 130. FIG. 7b shows the single suture 130 being hooked around the hook member 146 such that a portion of the suture 130 is vertically aligned parallel the Z-axis and along the outer side 132 of the coiled turns 128. FIGS. 7c to 7e depict the single suture 130 being wound through each of the coiled turns 128 via the helical path P of the device 110. As shown in FIG. 7f, the single suture 130 is wrapped about each of the turns 128 of the coiled member 112 such that suture 130 is frapped about itself, whereby the suture 130 becomes lashed to device 110. This lashing arrangement 134 is exactly the same as the frapping and wrapping arrangement 34 of the two sutures 30A and 30B of the first embodiment 10.

Figure 8:
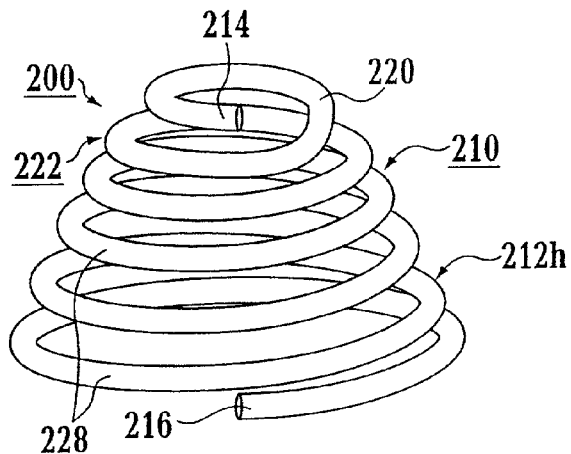
FIG. 8 is a perspective view of a helical suture anchoring device constructed in accordance with a third exemplary embodiment of the present invention, the device being shown in a coiled conically-shaped configuration and without a suture.

A third exemplary embodiment of the present invention is illustrated in FIG. 8. Elements illustrated in FIG. 8 which correspond to the elements described above with reference to FIGS. 1, 2c and 3 have been designated by corresponding reference numbers increased by two hundred. The third embodiment is constructed and operates in the same manner as the first embodiment, unless it is otherwise stated.

With reference to FIG. 8, the coiled member 212 of the helical suture anchoring and tensioning device 210 is exactly the same as the helical suture anchoring and tensioning device 10, except that the coiled helical configuration 222 is conically-shaped in a downward spiral. In operation, the suture(s) would not be pulled up along side the helix in a parallel relationship to the Z-axis, but rather along the outerside of the helix in an angled fashion.

Figure 9:
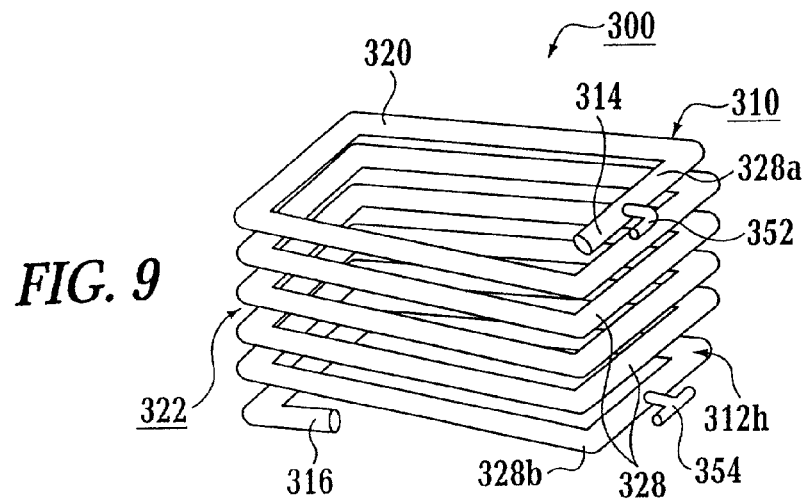
FIG. 9 is a perspective view of a helical suture anchoring device constructed in accordance with a fourth exemplary embodiment of the present invention, the device being shown in a coiled, rectangularly-shaped configuration and without a suture.

A fourth exemplary embodiment of the present invention is illustrated in FIG. 9. Elements illustrated in FIG. 9 which correspond to the elements described above with reference to FIGS. 1, 2c and 3 have been designated by corresponding reference numbers increased by three hundred. The fourth embodiment is constructed and operates in the same manner as the first embodiment, unless it is otherwise stated.

With reference to FIG. 9, the coiled member 312 of the helical suture anchoring and tensioning device 310 is exactly the same as the helical suture anchoring and tensioning device 10, except that the coiled helical configuration 322 is rectangularly-shaped. Additionally, the helical suture anchoring and tensioning device 310 includes an L-shaped hook member 352 which is integrally attached and positioned on the outer side 332 of the uppermost coiled turn 328a of the coiled member 312. The L-shaped hook member 352, which functions as a cleat, could be attached on the outer side 332 of any of the coiled turns 328 (i.e., the second or third coiled turn 328 from that of the uppermost coiled turn 328a). The L-shaped hook member 352 is used for attaching a small section of a single suture 330 to the L-shaped hook member 352 in order to facilitate the lashing process of suture 330 to device 310.

The helical suture anchoring and tensioning device 310 also includes a T-shaped hook member 354 which is integrally attached and positioned on the outer side 332 of the lowermost turn 328b of the coiled member 312. The T-shaped hook member 354, which functions as a cleat, may be used to aid in lashing or tensioning of the suture 330. As shown in FIG. 9, the L-shaped hook member 352 is in longitudinal alignment with the T-shaped hook member 354, which brings a suture 330 into close proximity to an incision site 356. The remaining elements of the coiled member 312 of device 310 are exactly the same as the component elements of device 10 of the first embodiment.

As indicated above, the L-shaped hook 352, or any other appendage adapted for connecting and/or tensioning a suture, may be placed and attached on any of the coiled turns 328 of the device 310. It should also be understood that any of the other suture anchoring and tensioning devices disclosed herein can be provided with the L-shaped hook member 352 and/or the T-shaped hook member 354.

Figure 10:
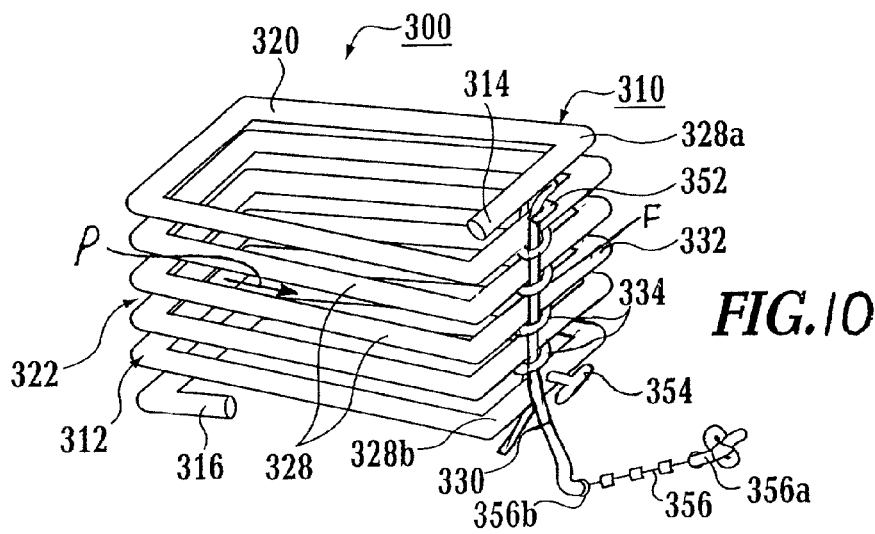
FIG. 10 is a perspective view of the helical suture anchoring device of FIG. 9 with a suture for suturing an incision by a surgeon.

In operation, the helical suture anchoring device 310 in combination with the single suture 330 may be used in various surgical procedures. For example, as shown in FIG. 10, the device 310 is used for securing the single suture 330 on an incision site 356 for a given surgical procedure. With reference to FIG. 10, the device 310 is positioned and placed in close proximity to an end stitch point 356b on the incision site 356 for securing the single suture 330 thereto. The single suture 330 is hooked around the L-shaped hook member 352 such that a portion of suture 330 is positioned parallel to the Z-axis along the outer side 332 of the coiled turns 328. The single suture 330 is then wound through each of the coiled turns 328 via the helical path P of device 310. Referring still to FIG. 10, the single suture 330 is wrapped about each of the coiled turns 328 of the coiled member 312 such that the suture 330 is frapped about itself, resulting in the lashing of suture 330 to the device 310. The frapping arrangement 334 is exactly the same as the frapping arrangement 134 of the single suture 130 of the second embodiment.

Figure 11:
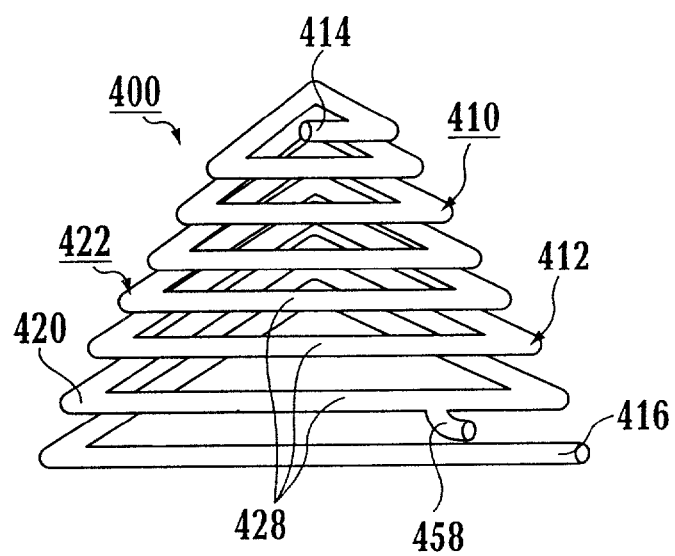
FIG. 11 is a perspective view of a helical suture anchoring device constructed in accordance with a fifth exemplary embodiment of the present invention, the device being shown in a coiled, triangularly-shaped configuration and without a suture.

A fifth exemplary embodiment of the present invention is illustrated in FIG. 11. Elements illustrated in FIG. 11 which correspond to the elements described above with reference to FIGS. 1, 2c and 3 have been designated by corresponding reference numbers increased by four hundred. The fifth embodiment is constructed and operates in the same manner as the first embodiment, unless it is otherwise stated.

With reference to FIG. 11, the coiled member 412 of the helical suture anchoring and tensioning device 410 is exactly the same as the helical suture anchoring and tensioning device 10, except that the coiled helical configuration 422 is pyramidally-shaped. Additionally, the helical suture anchoring and tensioning device 410 includes a flexible tab member 458 which is integrally attached in a vertically aligned orientation to the next lowermost turn 428c (see FIG. 11) of the coiled member 412. The tab member 458 helps prevent movement of a suture (not shown) backwards through the helical path P. The remaining elements of the coiled member 412 of device 410 are exactly the same as the component elements of device 10 of the first embodiment.

Figure 12:
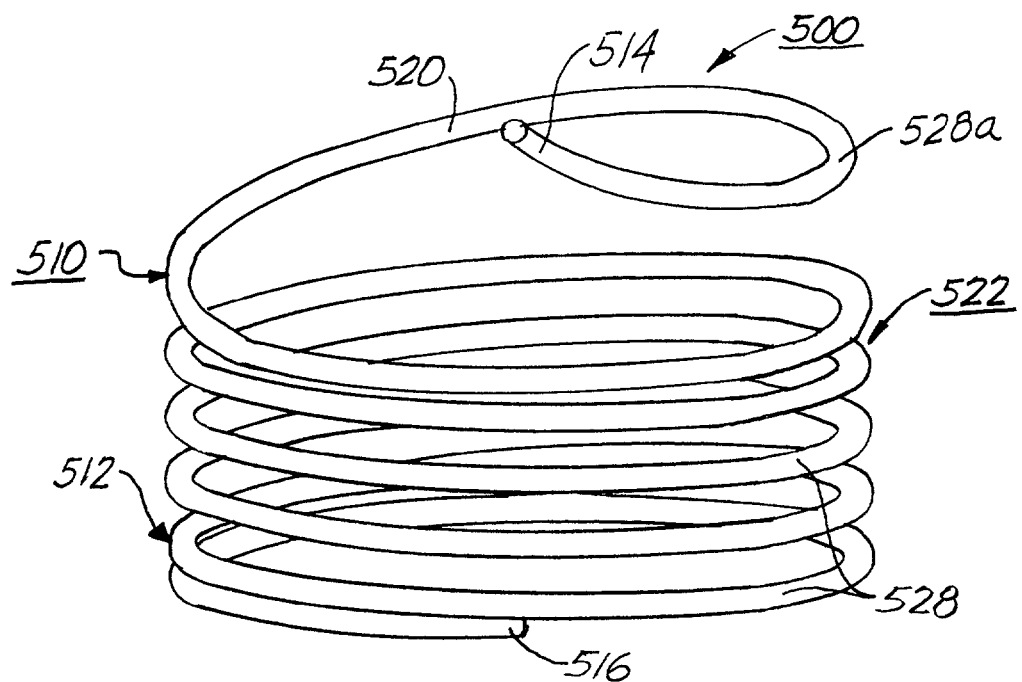
FIG. 12 is a perspective view of a helical suture anchoring device constructed in accordance with a sixth exemplary embodiment of the present invention, the device being shown in a coiled, oval-shaped configuration and without a suture.

A sixth exemplary embodiment of the present invention is illustrated in FIG. 12. Elements illustrated in FIG. 12 which correspond to the elements described above with reference to FIGS. 1, 2c and 3 have been designated by corresponding reference numbers increased by five hundred. The sixth embodiment is constructed and operates in the same manner as the first embodiment, unless it is otherwise stated.

With reference to FIG. 12, the coiled member 512 of the helical suture anchoring and tensioning device 510 is exactly the same as the helical suture anchoring and tensioning device 10, except that the coiled helical configuration 522 is oval-shaped, and the uppermost coiled turn 528a is further elevated and separated from the remaining coiled turns 528 for easily accessing device 510 with one or more sutures (not shown) in the lashing process.

Figure 13:
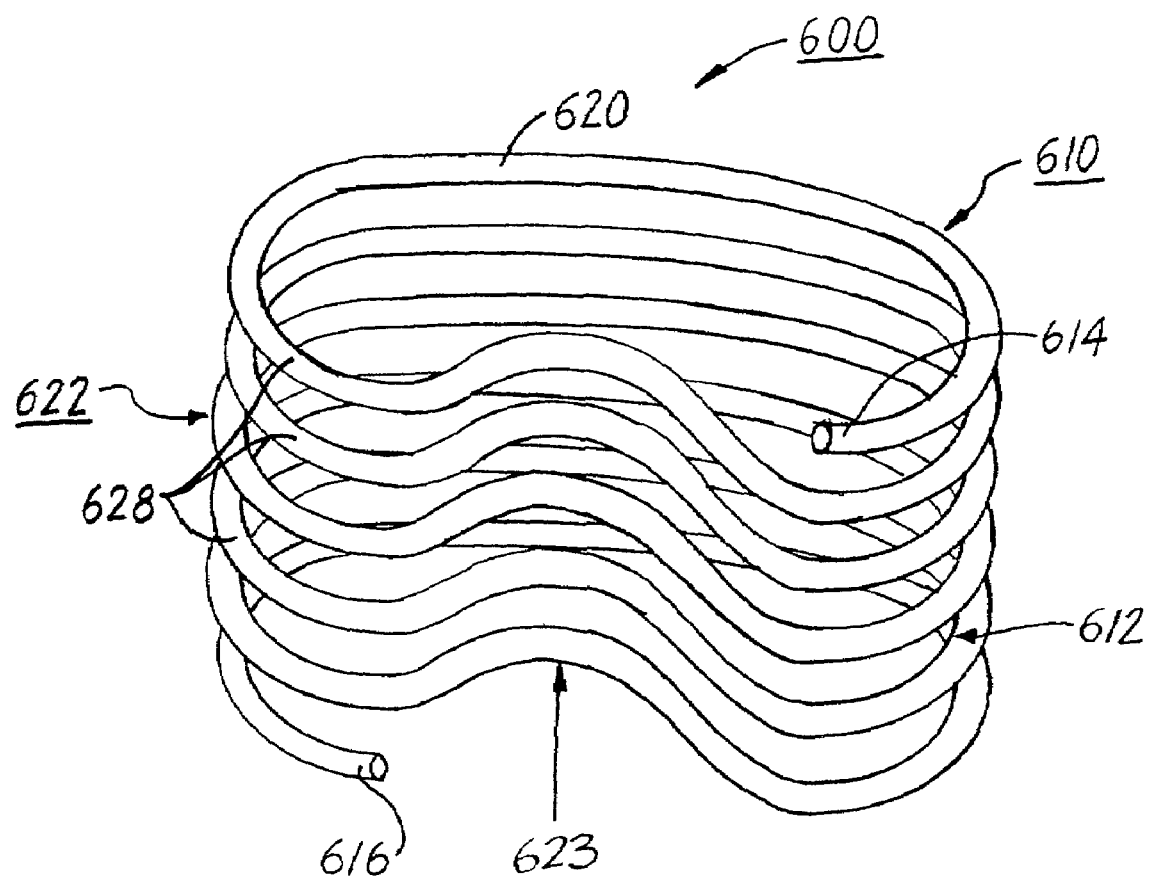
FIG. 13 is a perspective view of a helical suture anchoring device constructed in accordance with a seventh exemplary embodiment of the present invention, the device being shown in a coiled, U-shaped configuration and without a suture.

A seventh exemplary embodiment of the present invention is illustrated in FIG. 13. Elements illustrated in FIG. 13 which correspond to the elements described above with reference to FIGS. 1, 2c and 3 have been designated by corresponding reference numbers increased by six hundred. The seventh embodiment is constructed and operates in the same manner as the first embodiment, unless it is otherwise stated.

With reference to FIG. 13, the coiled member 612 of the helical suture anchoring and tensioning device 610 is exactly the same as the helical suture anchoring and tensioning device 10, except that the coiled helical configuration 622 is parabolic and/or U-shaped and has a cleft indentation 623 in order to position the lashing of the suture or sutures (not shown) closer (as compared to the other embodiments) to the center of gravity of the coiled member 612, thereby providing an increase in the stability of the lashed device 610. Furthermore, because the lashing of the suture(s) occurs within the confines of the device 610, the process of lashing the suture(s) to the device 610 is facilitated, and the bulk of the lashing remains with the device 610. Also, the U-shaped configuration helps to tension the sutures and approximate the wound because the cleft indentation 623 of the U-shaped configuration 622 holds the sutures close to each other over the wound site prior to the commencing of the lashing process.

Figure 14:
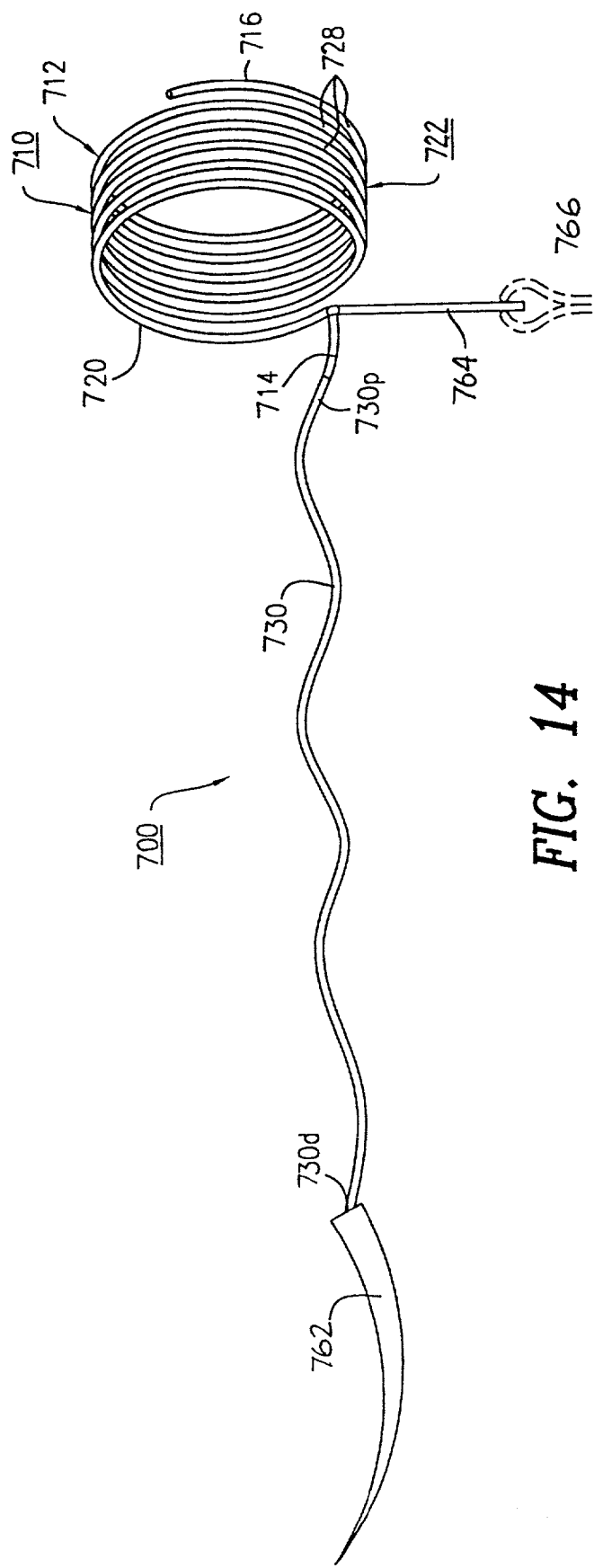
FIG. 14 is a perspective view of a helical suture anchoring device constructed in accordance with an eighth exemplary embodiment of the present invention, the device being integrally attached to a suture and the suture having a surgical needle attached thereto.

An eighth exemplary embodiment of the present invention is illustrated in FIG. 14. Elements illustrated in FIG. 14 which correspond to the elements described above with reference to FIGS. 1, 2c and 3 have been designated by corresponding reference numbers increased by seven hundred. The eighth embodiment is constructed and operates in the same manner as the first embodiment, unless it is otherwise stated.

With reference to FIG. 14, the distal end 714 of the coiled member 712 is connected to a proximal end 730p of a single suture 730 and a distal end 730d of the suture 730 is connected to a surgical needle 762. The distal end 714 also includes an integrally connected handle member 764, which is adapted to hold the coiled member 712 of device 710 in a stationary position by the use of a deployment aid 766 (i.e., a needle holder being shown in dotted). The remaining elements of the coiled member 712 of the helical suture anchoring and tensioning device 710 are exactly the same as the helical suture anchoring and tensioning device 10.

Figure 15:
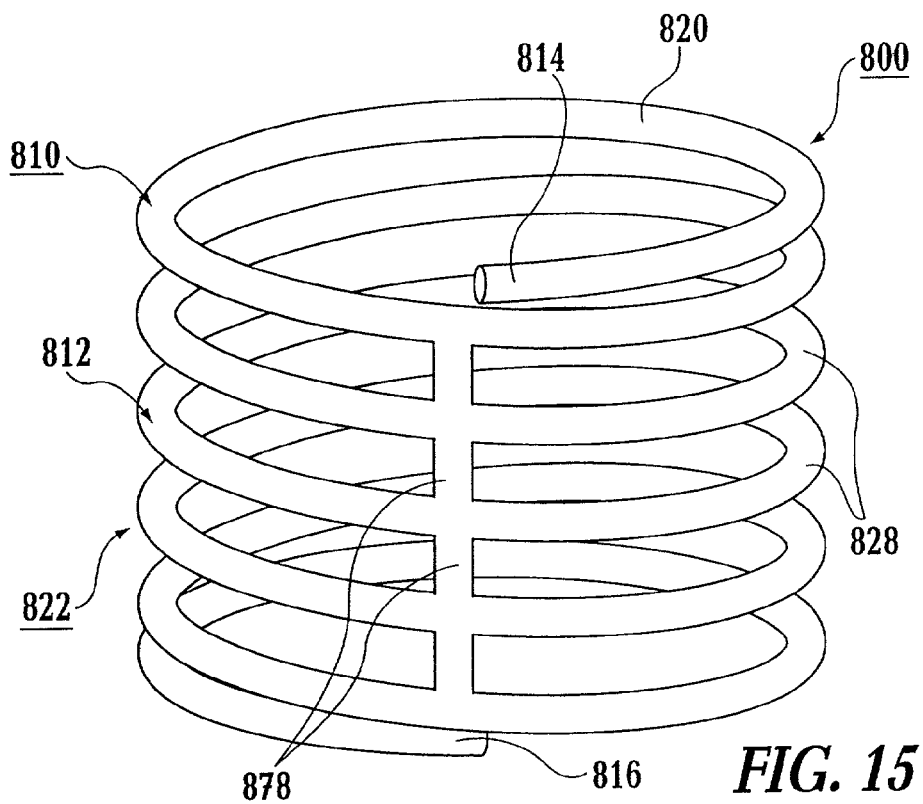
FIG. 15 is a perspective view of a helical suture anchoring device constructed in accordance with a ninth exemplary embodiment of the present invention, the device being shown without a suture but with a plurality of interlocking cross-bars connected between adjacent helically-configured coiled sections.
Figure 16:
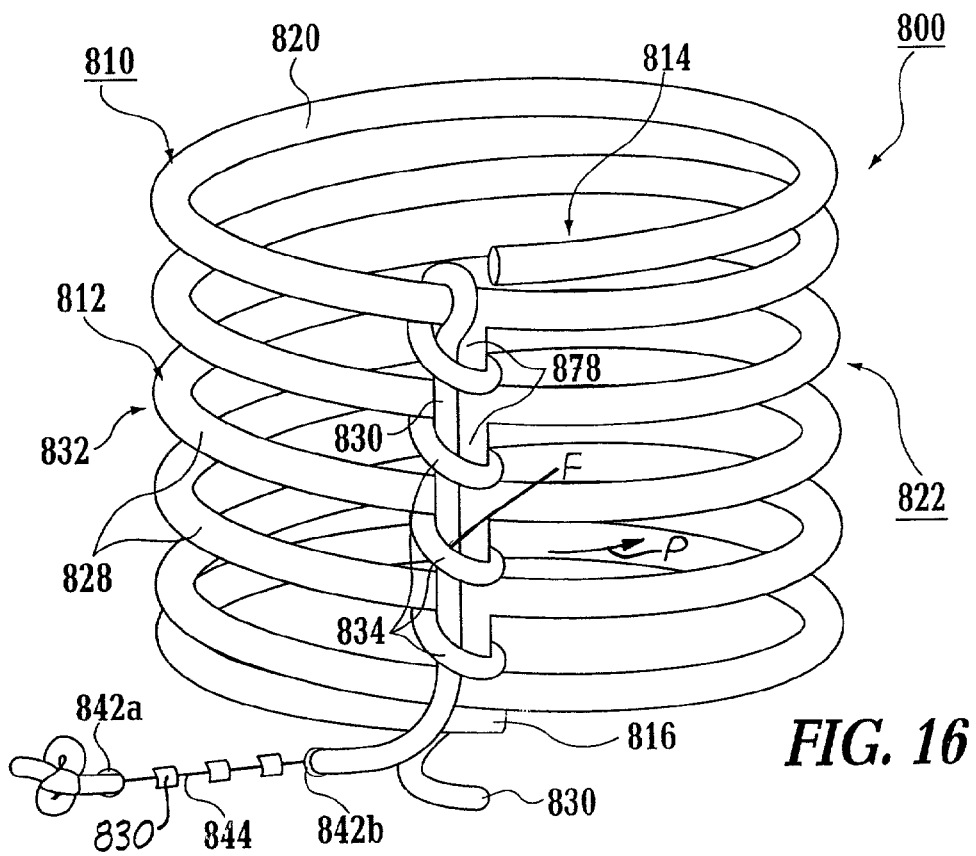
FIG. 16 is a perspective view of the helical suture anchoring device of FIG. 15 with a suture for suturing an incision by a surgeon.

A ninth exemplary embodiment of the present invention is illustrated in FIGS. 15 and 16. Elements illustrated in FIGS. 15 and 16 which correspond to the elements described above with reference to FIGS. 1, 2c and 3 have been designated by corresponding reference numbers increased by eight hundred. The ninth embodiment is constructed and operated in the same manner as the first embodiment, unless it is otherwise stated.

With reference to FIGS. 15 and 16, each of the helically-configured coiled sections 828 includes a longitudinally extending crossbar member 878. Each of the crossbar members 878 is integrally connected between an adjacent pair of the coiled sections 828. The crossbar members 878 are arranged at 360° intervals (i.e., one crossbar member 878 per revolution), whereby the crossbar members 878 are in longitudinal alignment with each other, as depicted in FIGS. 15 and 16. The suture 830 (see FIG. 16) may be lashed to the device 810 by each of the crossbars 878 and adjacent coiled sections 828, to form a suture frapping arrangement 834 on the coiled member 812. The frapping arrangement 834 is similar to that frapping arrangement shown in FIGS. 2a to 2c of device 10 of the first embodiment.

It should be understood that the embodiments described herein are merely exemplary and that a person skilled in the art may make many variations and modifications without departing from the spirit and scope of the present invention. All such variations and modifications are intended to be included within the scope of the invention as defined in the appended claims.

What is claimed is:

1. A method of anchoring a suture having a free end used in a surgical procedure, comprising the steps of:
 a) providing a coiled helical member having a first turn and a second turn adjacent to the first turn and separated therefrom so as to form a continuous helical space between the first and second turns, the coiled helical member being resilient so as to be movable between an extended position and a contracted position;

b) with the coiled helical member in its extended position, locating it in the proximity of a suturing site such that the second turn is between the suturing site and the first turn;

c) directing the free end of the suture away from the suturing site along an exterior surface of the coiled helical member past the second end thereof toward the first turn thereof;

d) wrapping the free end of the suture over the first turn of the coiled helical member so that the free end of the suture extends along an interior surface of the coiled helical member; and e) passing the free end of the suture through the continuous helical space formed between the first and second turns of the coiled helical member so as to trap the free end about a portion of the suture lying along the exterior of the coiled helical member against the first and second turns.

2. A method accordance with claim 1, wherein step (e) is followed by a step of wrapping the free end of the suture against the second turn thereby lashing the suture to the first and second turns of the coiled helical member.

3. A method in accordance with claim 2, wherein step (e) is performed so as to remove slack from the lashed suture.

4. A method in accordance with claim 1, wherein step (d) includes wrapping the free end of he suture against the first and second turns of the coiled helical member.

5. A method in accordance with claim 4, wherein step (d) includes wrapping the suture completely around the first and second turns of the coiled helical member.

6. A method in accordance with claim 1, wherein step (d) includes wrapping the free end of the suture completely around at least one of the first and second turns of the coded helical member.

7. A method in accordance with claim 1, wherein step (e) is performed by passing the free end of the suture through the entire continuous helical space between the first turn and the second turn.

8. A method in accordance with claim 1, wherein the first and second turns are equally distant from each other along their respective lengths.

9. A method in accordance with claim 1, wherein step (d) is performed after step (c) without an intervening wrapping step.

10. A method in accordance with claim 1, including a final step wherein the free end of the suture is in the proximity of the suturing site.

* * * * *